(12) United States Patent
Wang

(10) Patent No.: US 6,800,089 B1
(45) Date of Patent: Oct. 5, 2004

(54) MECHANICAL ATTACHMENT METHOD OF COVER MATERIALS ON STENTS

(75) Inventor: Chicheng Wang, Newport Beach, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 267 days.

(21) Appl. No.: 09/583,263

(22) Filed: May 31, 2000

(51) Int. Cl.$^7$ ................................................ A61F 2/06
(52) U.S. Cl. ................................ 623/1.44; 623/1.13
(58) Field of Search ................ 623/1.1, 1.42–1.49, 623/1.28, 1.53, 1.13, 1.32

(56) References Cited

U.S. PATENT DOCUMENTS

| | | | | |
|---|---|---|---|---|
| 4,164,045 A | * | 8/1979 | Bokros et al. ............. 623/1.28 |
| 4,441,215 A | * | 4/1984 | Kaster ....................... 623/1.53 |
| 4,776,337 A | * | 10/1988 | Palmaz ..................... 623/1.11 |
| 5,053,048 A | * | 10/1991 | Pinchuk ...................... 623/1.1 |
| 5,421,955 A | | 6/1995 | Lau et al. ..................... 216/48 |
| 5,421,955 A | | 6/1995 | Lau et al. ..................... 216/48 |
| 5,423,885 A | * | 6/1995 | Williams ...................... 623/1.1 |
| 5,514,154 A | | 5/1996 | Lau et al. ................... 606/195 |
| 5,569,295 A | | 10/1996 | Lam ........................... 606/198 |
| 5,578,075 A | * | 11/1996 | Dayton ....................... 623/1.1 |
| 5,593,434 A | | 1/1997 | Williams ....................... 623/1 |
| 5,603,721 A | | 2/1997 | Lau et al. ................... 606/195 |
| 5,618,299 A | | 4/1997 | Khosravi et al. ........... 606/198 |
| 5,637,113 A | | 6/1997 | Tartaglia et al. ................ 623/1 |
| 5,649,952 A | | 7/1997 | Lam ........................... 606/198 |
| 5,693,085 A | | 12/1997 | Buirge et al. ................... 623/1 |
| 5,700,285 A | * | 12/1997 | Myers et al. ................. 623/1.1 |
| 5,700,286 A | | 12/1997 | Tartaglia et al. ................ 623/1 |
| 5,718,973 A | * | 2/1998 | Lewis et al. ............... 623/1.32 |
| 5,725,572 A | | 3/1998 | Lam et al. ...................... 623/1 |
| 5,728,158 A | | 3/1998 | Lau et al. ...................... 632/12 |
| 5,735,893 A | | 4/1998 | Lau et al. ....................... 623/1 |
| 5,759,192 A | | 6/1998 | Saunders .................... 606/194 |
| 5,766,238 A | | 6/1998 | Lau et al. ....................... 623/1 |
| 5,843,172 A | * | 12/1998 | Yan ............................ 623/1.1 |
| 5,849,037 A | | 12/1998 | Frid .............................. 623/1 |
| 5,876,432 A | | 3/1999 | Lau et al. ....................... 623/1 |
| 5,891,191 A | | 4/1999 | Stinson ......................... 623/1 |
| 5,897,911 A | | 4/1999 | Loeffler ..................... 427/2.25 |
| 5,925,075 A | * | 7/1999 | Myers et al. ............... 623/1.13 |
| 6,334,868 B1 | * | 1/2002 | Ham ......................... 623/1.13 |

* cited by examiner

*Primary Examiner*—Julian W. Woo
(74) *Attorney, Agent, or Firm*—Fulwider Patton Lee & Utecht, LLP.

(57) ABSTRACT

The present invention relates to a stent comprising a structural support and a polymeric film or sheet or tube. The structural support comprises an outer surface that is roughened patterned. The polymeric film or sheet or tube is retained to the structural support by the roughened or patterned outer surface of the structural support.

14 Claims, 6 Drawing Sheets

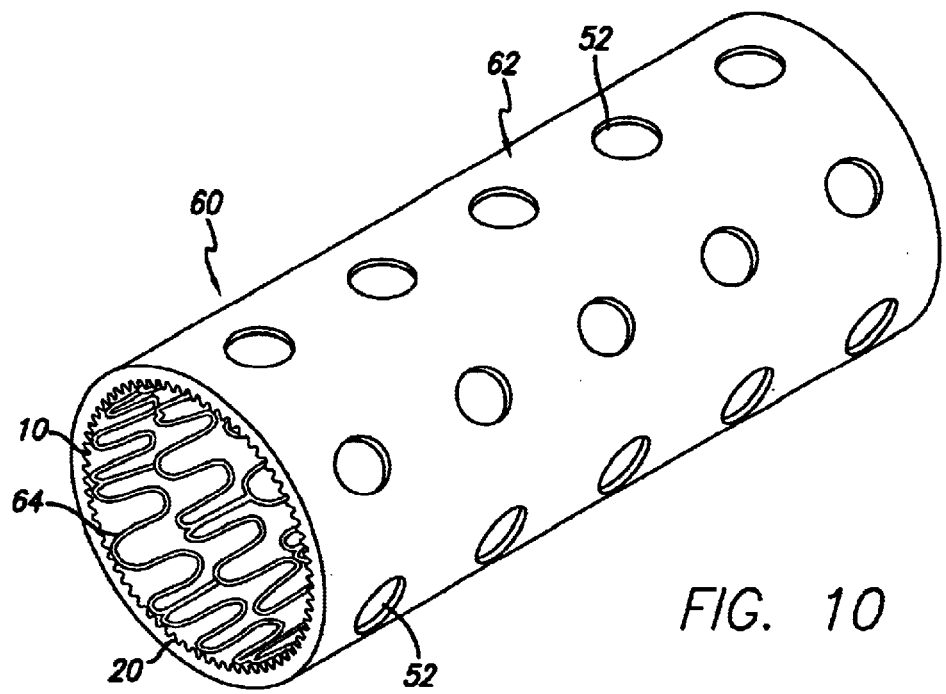
FIG. 10
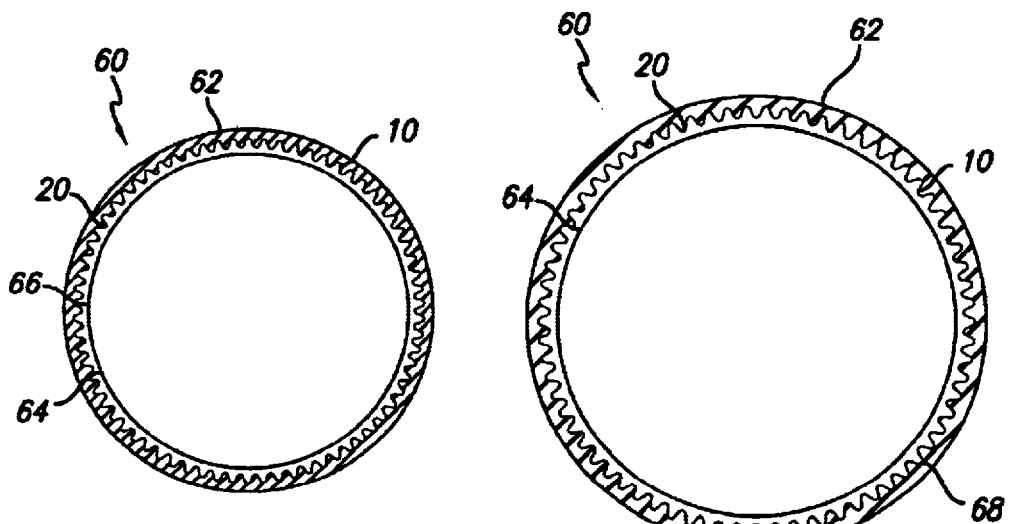
FIG. 10A
FIG. 10B

MECHANICAL ATTACHMENT METHOD OF COVER MATERIALS ON STENTS

BACKGROUND OF THE INVENTION

The present invention relates to a method for securing covering materials onto a stent. The present invention also relates to a stent having a roughened or patterned surface. The present invention further relates to a device comprising a stent having a roughened or patterned surface and to a covering on the stent.

Stents are implanted within vessels in living beings in order to maintain patency of the vessels and to prevent collapse of the vessels. Stents also impede restenosis. Implantation of a stent is typically accomplished by mounting the stent onto an expandable portion of a balloon catheter, and maneuvering the catheter through the vasculature of the living being so as to position the stent at a desired location within a vessel lumen. Implantation also includes inflating the balloon to expand the stent so as to engage a wall of the lumen. The stent automatically locks into an expanded configuration allowing the balloon to be deflated and the catheter to be removed in order to complete the implantation procedure.

In some instances, it is desirable to provide localized pharmacological treatment of a vessel at the site supported by the stent. It has been found convenient to utilize the stent as a delivery vehicle for such purposes. However, because of the mechanical strength that is required to properly support vessel walls, stents are typically constructed of metallic materials which are not capable of releasing or carrying drugs. Various polymers are capable of carrying and releasing drugs but generally do not have the requisite mechanical strength. One solution to this problem has been a coating of a stent's metallic structure with a polymer material in order to provide the stent with properties that permit the stent to support adequate mechanical loads and to deliver drugs.

Various approaches have been used to join polymers to metallic stents, including dipping, spraying and conforming processes. Such methods have failed to provide an economically viable method of applying a very even coating of polymer on the stent surfaces or to economically apply different thicknesses or different polymers in different areas on the same stent.

Some covers are not meant to be permanently adhered to the stent. These temporary covering materials are adhered to the stent by adhesives. A silicone based, two component adhesive has typically been applied to distal and proximal ends of the stents. One problem with the use of adhesive is a lack of compatibility. Adhesive residues on the stent inner surface are not biocompatible with the vessel wall and can, in some instances, cause inflammation of the vessel wall. One other problem with the use of adhesives is related to a non-uniform stent deployment at regions where the adhesive covers the stent. In some instances, the stent is not deployed in a fully lengthened position due to strong adhesive bonds between the adhesive and the stent.

U.S. Pat. No. 5,637,113, which issued Jun. 10, 1997, to Taraglia et al. describes a metallic stent which is wrapped with a polymeric film. The polymeric film is capable of carrying and releasing therapeutic agents. The polymeric film is secured to the metallic stent by a mechanism such as adhesive bonding. The adhesive is a copolymer of poly-L-lactic acid (L-PLA) and polycaprolactone (PCL). Other adhesives, heat bonding, solvent bonding and one or more mechanical fasteners, such as a metal clip are also suitable.

SUMMARY OF THE INVENTION

One product aspect of the present invention comprises a stent that comprises a structural support. The structural support comprises an outer surface that is roughened or patterned. The stent also comprises a polymeric film or sheet or tube that overlays the structural support. The polymeric sheet or film is retained to the structural support by the roughened or patterned outer surface.

Another embodiment of the present invention comprises a retaining system. The retaining system comprises a stent and a roughened or patterned surface on the stent.

One method aspect of the present invention is a method for adhering a polymeric sheet to a stent structural member. The method comprises providing a stent structural member with an outer surface. The method also comprises providing a polymeric sheet or tube. The method further comprises roughening or patterning the outer surface of the stent structural member and retaining the polymeric sheet or tube on the stent structural member at the roughened or patterned area.

Another embodiment of the present invention comprises a stent assembly. The stent assembly comprises a structural member with an outer surface that is roughened or texturized. The stent assembly also comprises a polymeric sleeve. The polymeric sleeve is retained to the structural member by the roughened or texturized surface.

One other embodiment of the present invention comprises a stent assembly. The stent assembly comprises a structural member with an outer surface that is roughened or textured. The stent assembly also comprises a polymeric sheet. The polymeric sheet is retained to the structural member by the roughened or textured surface.

DESCRIPTION OF THE DRAWINGS

FIG. 10 illustrates a perspective view of one embodiment of a stent-textured surface-polymeric cover wherein the polymeric cover is a sleeve and is drug loaded.

FIG. 10A illustrates the stent-textured surface-polymeric cover of FIG. 10 in an unexpanded position.

FIG. 10B illustrates the stent-textured surface-polymeric cover of FIG. 10 in an expanded position.

DETAILED DESCRIPTION

Figure 5:
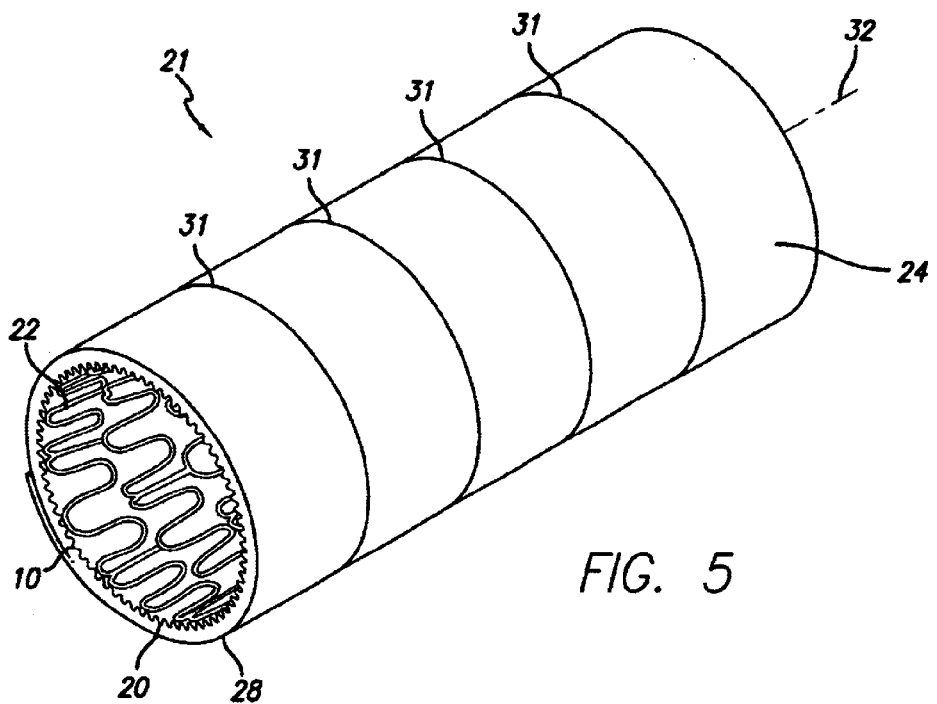
FIG. 5 illustrates a perspective view of one embodiment of an expandable stent-textured surface-polymeric cover of the present invention.
Figures 5A, 5B:
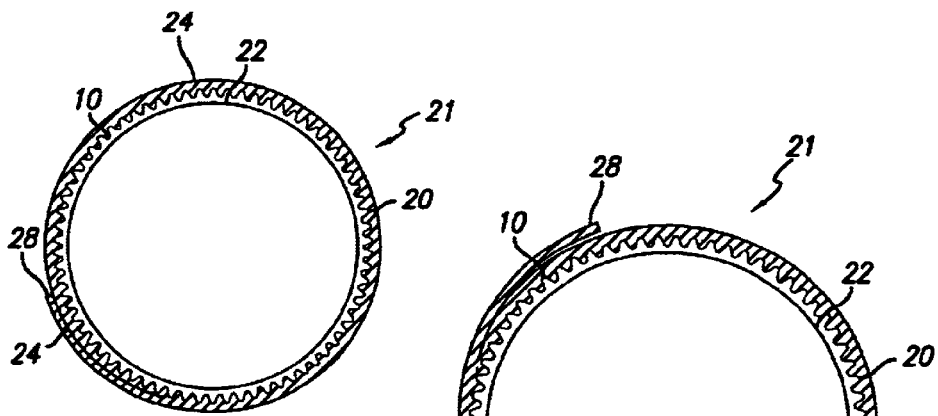
FIG. 5A illustrates in cross-section the expandable stent-textured surface-polymeric cover of the present invention in an unexpanded position.
FIG. 5B illustrates in cross-section the expandable stent-textured surface-polymeric cover of the present invention in an expanded position.

One product aspect of the present invention includes a stent, one embodiment of which is illustrated at 21 in FIG. 5, with a surface area 26, shown in Fig. 5A and a sharp texture design 20 on at least a portion of the surface area 26. The texture design is effective for retaining coverings such as is shown at 24 in FIG. 5 on the stent without applying any adhesives to the stent surface. The texture designs usable in the present invention impart sufficient friction to the stent surface, uniformly over the texturized surface, and impede the polymer materials covering the stent from shifting during the delivery and deployment procedures.

A use of textured patterns alone to retain a covering on the stent is a significant departure from conventional technology which employs adhesives to secure covering materials to a stent. Typically, a silicone-based, two component adhesive has been applied to distal and proximal ends of the stents. The use of adhesives presents biocrompatibility problems in use of the stent. The adhesives also impose a risk of leaving adhesive residues on a stent inner surface. The adhesives create a problem with non-uniform stent deployment at the adhesive bonding regions and contribute to stent shortening partially due to a strong adhesion. The present invention eliminates a requirement to use any adhesive at all.

Figure 4:
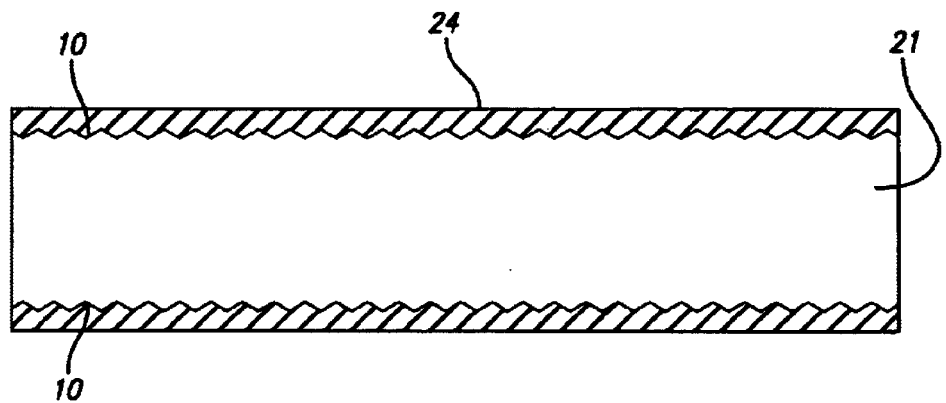
FIG. 4 illustrates a cross-sectional view of one embodiment of a textured pattern covered with a polymeric cover.

The textured patterns permit an interface mechanical retaining of the cover onto the stent. One cross-sectional view of this "retaining" is shown at 10 in FIG. 4. The textured patterns are impartible on a stent of virtually any biocompatible material. Metals such as stainless steel, Ni-Ti, platinum, Nitinol, tantalum or gold may be used. A plastic that is biocompatible may be used.

Figure 1:
FIG. 1 illustrates a side view of one triangular surface pattern embodiment of the present invention.

One triangular surface pattern is illustrated at 9 in FIG. 1. A spiked surface pattern is illustrated at 20 in FIG. 2. A square pattern is illustrated at 30 in FIG. 3. Stents of the present invention may be fabricated with any one of these patterns or with a combination of the patterns. For instance, a stent may be fabricated with a triangular pattern at a distal end and a proximal end and the square pattern in the middle of the stent. A stent may be fabricated with a triangular pattern and spiked pattern intermixed. A stent may be fabricated with a spiked and square pattern intermixed.

The raised patterns have a height of about 0.01 to 0.005 inches. For many embodiments, the patterns are not sharply defined but are blunted or rounded at the edges. The patterned or roughened surface covers the entire outer surface of the stent for some embodiments. For other embodiments, the patterned or roughened surface covers the outer surface of the stent at ends of the stent.

Figure 3:
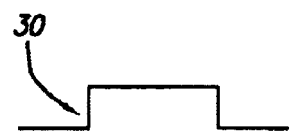
FIG. 3 illustrates a side view of one square surface pattern embodiment of the present invention.
Figure 2:
FIG. 2 illustrates a side view of one spiked surface pattern embodiment of the present invention.

The protrusions 9, 20 and 30, in FIGS. 1, 2 and 3, are, for many embodiments, made of the same material as the stent. For some embodiments, the protrusions 9, 20 and 30 are made of a coating material on the stent. The surface textures are formed by methods that utilize one or more of plasma techniques, corona techniques, molding, casting, lazing, etching, machining or any other cutting technique that changes the surface texture of the body or that roughens the surface.

One stent embodiment of the present invention, illustrated generally at 21 in FIG. 5, comprises an expandable stent structural member 22 and a planar sheet or film 24 of polymeric material. The structural member 22 is shown in an unexpanded state in cross-section in FIG. 5A and in an expanded state in FIG. 5B. In a first embodiment, the polymeric planar sheet or film 24 is attached to the stent member, which is metal, at one portion of raised surface of the textured area. The attachment occurs through use of the textured pattern or roughened surface of the present invention.

The film or planar sheet 24 has a free end and for some embodiments, defines one or more slits 31 in the polymeric film transverse to the axis 32 of the stent in order to accommodate possible uneven expansion of the stent structural member 22. The planar sheet of polymeric material 24 is adapted to uncoil and to expand in order to match expansion of the stent structural member 22. In particular, a strip of an inside surface of the polymeric film 24 is textured in order to adhere an end 28 of the polymeric sheet to the rolled sheet 24, as shown in FIGS. 5, 5A, and 5B.

Figure 6:
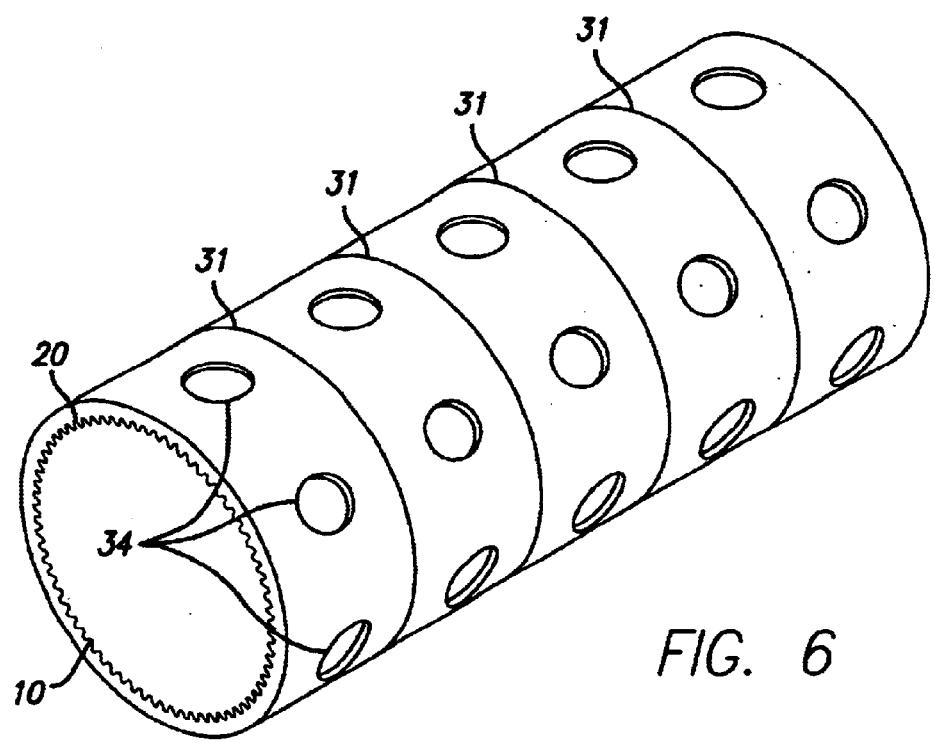
FIG. 6 illustrates a perspective view of one embodiment of an expandable stent-textured surface-polymeric cover wherein the stent and polymeric cover define apertures.

The planar sheet of polymer material 24 is a solid sheet for some embodiments but for other embodiments, the sheet includes a surface that defines a plurality of apertures 34 of various sizes and shapes in order to promote rapid endothelialization, such as illustrated in FIG. 6. The stent is mountable on a balloon dilatation catheter for deployment of the stent in the vasculature of a patient.

Figure 9A:
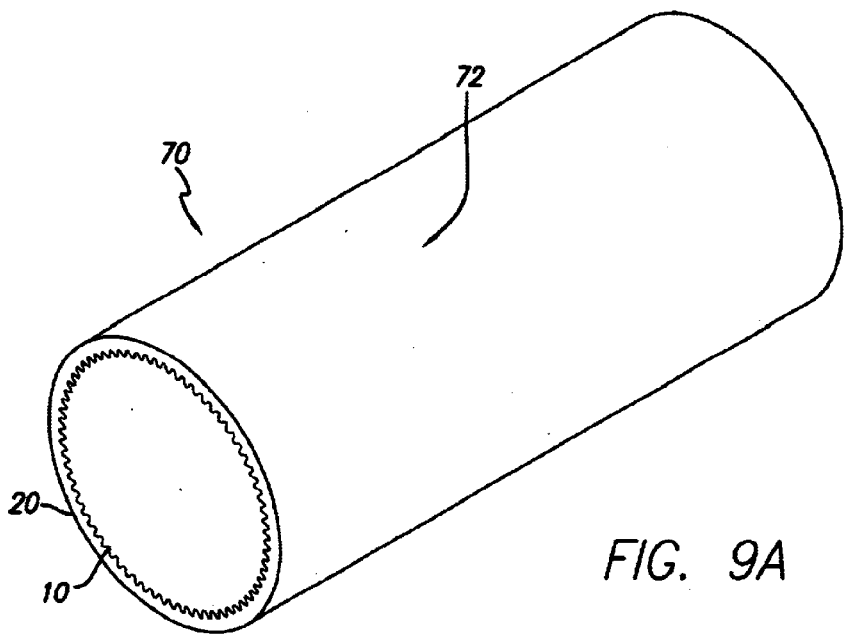
FIG. 9A illustrates an expandable tubular cover embodiment of the textured surface-polymeric cover of the present invention.
Figure 9B:
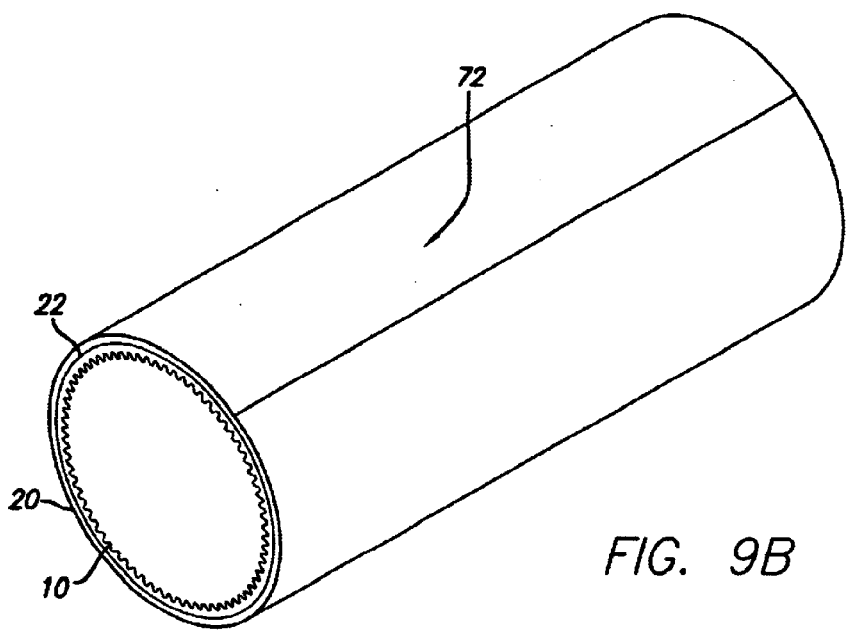
FIG. 9B illustrates a stent-textured surface-expandable tubular cover embodiment of the present invention.

Another embodiment of the present invention, illustrated generally at 70 in FIG. 9A includes a tubular, expandable main body 72, which is textured in accordance with the present invention on an outer annular surface. A stent 22 is positioned within the tubular, expandable main body 72, as is shown in FIG. 9B.

Figure 7:
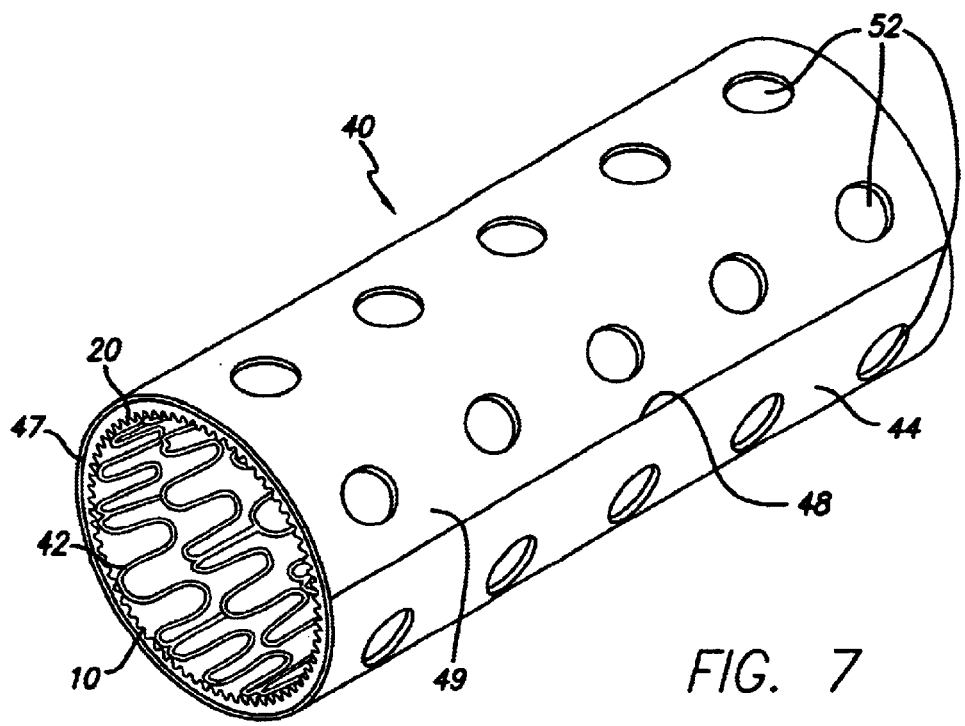
FIG. 7 illustrates a perspective view of one embodiment of a stent-textured surface-polymeric cover wherein the polymeric cover is drug loaded.
Figure 8A:
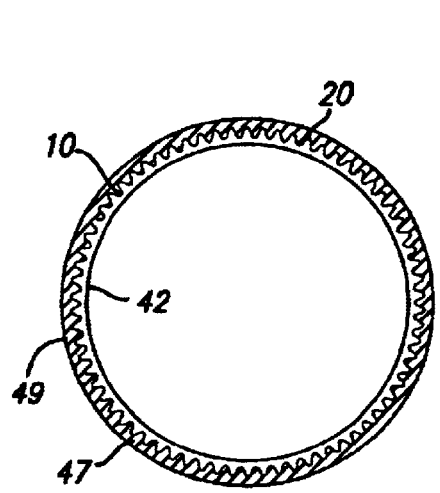
FIG. 8A illustrates in cross-section the stent-textured surface-polymeric cover of FIG. 7 in an expanded position.
Figure 8B:
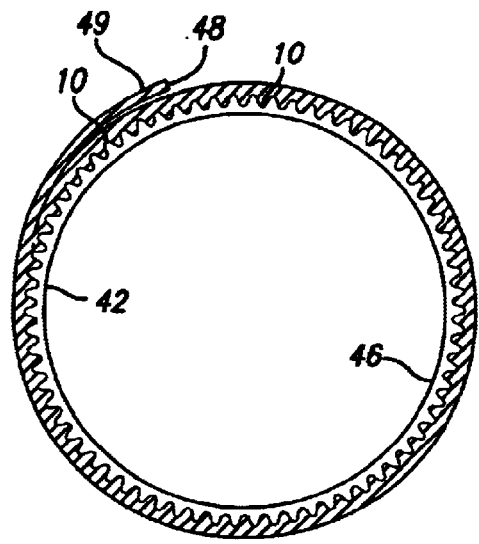
FIG. 8B illustrates in cross-section the stent-textured surface-polymeric cover of FIG. 7 in an expanded position.

In another embodiment of the present invention, illustrated generally in FIG. 7, the stent is drug laden so that the stent comprises a stent metal structural member 42 and a planar sheet or film of polymeric material 44. The film of polymeric material 44 has a first end 46 of a first layer 47 of polymeric material and a second end 48 of a second layer 49 overlapping the first end 46 and attached to the first layer 47 of the polymeric film 44. Attachment of the first layer 47 of the polymeric film is accomplished by the textured or roughened surface of the present invention on the stent structural member 42.

In this embodiment, the planar sheet of polymeric material is wrapped circumferentially and cinched tightly as a sleeve on the stent structural member. The textured surface on the stent member retains the polymeric material.

For some stent embodiments, illustrated in FIGS. 7 and 10, the polymeric material defines apertures such as are shown at 52, formed within the polymeric material. The apertures 52 impart a porousness to the polymeric material and allow blood flow through the stent structural member to a vessel wall such as for oxygenation and nutrient exchange to the vessel wall in order to prevent a decreased surface area for purposes of reducing thromobgenicity. The apertures 52 improve flexibility of the polymeric material allowing the stent segment to be more easily rolled and coiled during expansion of the stent structural member and also to facilitate the process of cell growth over the surface of the stent.

In another embodiment, illustrated at 60 in FIGS. 10, 10A, and 10B, a polymeric material is formed as a seamless tube or sleeve 62 that fits tightly around an unexpanded stent structural member, shown in cross-section in FIG. 10A. The seamless polymeric tube 62 is adhered to the stent 64 by the textured surface of the present invention which is imparted to the structural member 64. The sleeve 62 and structural member 64 are expandable to an expanded configuration, shown in cross-section in FIG. 10B. The sleeve 62 includes an inner layer 66 and an outer layer 68 that overlays the inner layer 66. The outer layer 68 is loaded with drugs after adherence to the stent structural member 64. Unlike adhesives which present problems in expansion, a use of the textured or roughened surface of the present invention for adherence presents no expansion problems.

A primary function of the outer layer 68 of the sheet or sleeve of polymeric material is to deliver therapeutic drugs, such as drugs to help thrombosis and/or restinosis. The inner layer 66 of polymeric material is selected from a group of polymers that include thermoplastic and elastomeric polymers so that the polymeric film can stretch or deform radially when the structural member 62 is expanded.

The planar sheet of polymeric material has a surface that defines a plurality of apertures 52 of various sizes and shapes to promote rapid endothelialization similar to the embodiment illustrated in FIG. 6. The stent is mounted on a balloon dilatation catheter for deployment of the stent in the vasculature of a patient.

In each of these embodiments, the stent structural member is implantable within a vessel in a contracted state and is expandable to maintain patency of the vessel and to allow fluid flow throughout the vessel. The metal structural member can, for example, be formed from a metal selected from a group of metals that includes stainless steel, MP35N, elastonite (nitinol), tantalum gold-titanium alloy, platinum-radium alloy, gold and magnesium although the stent structural member is also formable of suitable non-metallic materials. MP35N and MP20N are trade names for alloys of cobalt, nickel, chromium and molybdenum available from Standard Pressed Steel Co. of Jenkintown, Pa. MP35N consists of 35% cobalt and 35% nickel. MP20N consists of 50% cobalt and 50% molybdenum.

The polymeric material is selected from thermoplastic and elastomeric polymers. In one embodiment, the polymeric material is a material available under the trade name C-Flex from Concept Polymer Technologies of Largo, Fla. In another embodiment, the polymeric material is ethylene vinyl acetate (EVA). In another currently available embodiment, the polymeric material is a material available under the trade name, Biospan. Other suitable polymeric materials include latexes, urethanes, polysiloxanes, and modified styrene-ethylenelbutylene styrene block copolymers (SEBS), expandable polytetrafluoroethylene linear aliphatic polyesters.

The polymeric material is used to make a layer that has a thickness within a range of about 0.002 to about 0.020 inches. For some embodiments, the polymeric material is bioabsorbable and is loaded or coated with a therapeutic agent or drug, including, but not limited to antiplatlets, antithrombins, cytostatic and antiproliferative agents, for example, to reduce or to prevent restenosis in the vessel being treated. A therapeutic agent or a drug is preferably selected from the group of therapeutic agents or drugs that include sodium heparin, low molecular weight heparin, hirudin, argatrobin, forskolin, vapiprost, prostacyclin and prostacyclin analogues, dextran, D-phe-pro-arg-chloromethylketone, dipyridamole, glycoprotein, IIB/IIIA platelet membrane receptor antibody, recombinant hirudin, thrombin inhibitor, angiopeptin, angiotensin converting enzyme inhibitors, such as captopril available from Squibb; Cilazapril available from Hoffrnan-La Roche; or Lisinopril available form Merck, calcium channel blockers, colchicine, fibroblast growth factor antagonists, fish oil, omega 3-fatty acid, histamine antagonists, HMG-CoA reductase inhibitor, methotrexate, monoclonal antibodies, nitroprussid, phosphodiesterase inhibitors, prostaglandin inhibitor, seramin, serotonin blockers, steroids, thioprotease inhibitors, trizaolo pyrimidine and PDFG antagonists, alpha-interferon and genetically engineered epithelial cells and combinations thereof. While the foregoing therapeutic agents have been used to prevent or treat restinosis and thrombosis, they are provided by way of example and are not meant to be limiting, as other therapeutic drugs may be developed which are equally applicable for use with the present invention.

While particular forms of the invention have been illustrated and described, various modifications can be made without departing from the spirit and scope of the invention. Accordingly, it is not intended that the invention be limited except by the appended claims.

What is claimed is:

1. A stent, comprising:
   a structural support having an outer surface that includes a pattern of raised squares; and
   a polymeric film or sheet or tube that overlays the structural support wherein the polymeric film or sheet or tube is retained to the structural support by the raised squares.

2. The stent of claim 1, wherein the polymeric film comprises one or more of ethylene vinyl acetate, latexes, urethanes, polytetrafluoroethylene, polysiloxanes, and modified styrene-ethylene/butylene styrene block copolymers.

3. The stent of claim 1, wherein the polymeric film comprises one or more drugs.

4. The stent of claim 1, wherein the polymeric film defines apertures.

5. The stent of claim 1, wherein the polymeric film is an expandable sleeve.

6. A stent, comprising:
   a structural support having a first unexpanded configuration and a second expanded configuration and an outer surface that is roughened or patterned and at least partially covered with one or more of raised triangles, spikes and raised squares;
   a polymeric film or sheet or tube that overlays the structural support, the polymeric film or sheet or tube having a first end and a second end, the first end attached to the structural support and wrapped around the structural support such that a first layer and second layer are formed, the second layer overlapping the first end when the structural support is in the unexpanded configuration; and
   wherein the polymeric film or sheet or tube is retained to the structural support by the roughened or patterned outer surface and fills in gaps in the outer surface such that the exterior of the stent is smooth.

7. The retaining system of claim 6, wherein the squares or triangles or spikes are raised from about 0.001 inch to 0.005 inch.

8. The stent assembly of claim 6, wherein the structural support and polymeric film are expandable.

9. The stent assembly of claim 6, wherein the polymeric film contains drugs.

10. A stent, comprising:
    a structural support having an outer surface that includes a pattern of raised triangles; and
    a polymeric film or sheet or tube that overlays the structural support wherein the polymeric film or sheet or tube is retained to the structural support by the raised triangles.

11. The stent assembly of claim 10, wherein the structural support and the polymeric film are expandable.

12. The stent assembly of claim 10, wherein the polymeric film contains drugs.

13. A stent, comprising:

a structural support having an outer surface that includes a pattern of raised spikes; and a polymeric film or sheet or tube that overlays the structural support wherein the polymeric film or sheet or tube is retained to the structural support by the raised spikes.

14. A stent, comprising:

a structural support having a first unexpanded configuration and a second expanded configuration and an outer surface that is roughened or patterned and at least partially covered with raised squares;

a polymeric film or sheet or tube that overlays the structural support, the polymeric film or sheet or tube having a first end and a second end, the first end attached to the structural support and wrapped around the structural support such that a first layer and second layer are formed, the second layer overlapping the first end when the structural support is in the unexpanded configuration; and wherein the polymeric film or sheet or tube is retained to the structural support by the roughened or patterned outer surface and fills in gaps in the outer surface such that the exterior of the stent is smooth.

\* \* \* \* \*

UNITED STATES PATENT AND TRADEMARK OFFICE
CERTIFICATE OF CORRECTION

PATENT NO.    : 6,800,089 B1
DATED         : October 5, 2004
INVENTOR(S)   : Chicheng Wang It is certified that error appears in the above-identified patent and that said Letters Patent is hereby corrected as shown below:

Title page,
Item [57], ABSTRACT, delete "roughened patterned" and insert -- roughened or patterned --.

Column 3,
Line 24, delete "biocrompatibility" and insert -- biocompatibility --.

Column 5,
Line 43, delete "styrene-ethylenebutylene" and insert -- styrene-ethylene/butylene --.
Line 62, delete "Hoffrnan" and insert -- Hoffman --.

Signed and Sealed this

Third Day of May, 2005

JON W. DUDAS
*Director of the United States Patent and Trademark Office*